United States Patent
Mantinband et al.

(10) Patent No.: US 11,382,548 B2
(45) Date of Patent: Jul. 12, 2022

(54) APPARATUS, SYSTEM, AND METHODS FOR URINALYSIS

(71) Applicant: RENALSENSE LTD., Jerusalem (IL)

(72) Inventors: Jack Yehoshua Mantinband, Efrata (IL); Mor Grinstein, Modi'in (IL); Michael Adler, Kfar Vradim (IL)

(73) Assignee: RENALSENSE LTD., Jerusalem (IL)

( * ) Notice: Subject to any disclaimer, the term of this patent is extended or adjusted under 35 U.S.C. 154(b) by 714 days.

(21) Appl. No.: 15/536,004

(22) PCT Filed: Dec. 21, 2015

(86) PCT No.: PCT/IL2015/051237
§ 371 (c)(1),
(2) Date: Jun. 14, 2017

(87) PCT Pub. No.: WO2016/103256
PCT Pub. Date: Jun. 30, 2016

(65) Prior Publication Data
US 2017/0367636 A1    Dec. 28, 2017

Related U.S. Application Data

(60) Provisional application No. 62/095,115, filed on Dec. 22, 2014.

(51) Int. Cl.
*A61B 10/00*    (2006.01)
*A61B 5/1473*   (2006.01)
(Continued)

(52) U.S. Cl.
CPC ............ *A61B 5/201* (2013.01); *A61B 5/1473* (2013.01); *A61B 5/1495* (2013.01);
(Continued)

(58) Field of Classification Search
None
See application file for complete search history.

(56) References Cited

U.S. PATENT DOCUMENTS 4,338,024 A * 7/1982 Bolz .................... G01N 15/147
                                                 356/23
4,343,316 A   8/1982 Jespersen
(Continued)

FOREIGN PATENT DOCUMENTS

CN    201260721 Y    6/2009
CN    102792148 A   11/2012
(Continued)

OTHER PUBLICATIONS

Simerville, Jeff A. et al. "Urinalysis: a comprehensive review." American family physician 71.6 (2005): 1153-1162.
(Continued)

*Primary Examiner* — Jay B Shah
(74) *Attorney, Agent, or Firm* — Leason Ellis LLP

(57) ABSTRACT

Described is an apparatus for inline urine analysis comprising a control unit and at least one image capture unit comprising an image sensor and an optical assembly. The apparatus is configured to be coupled with an indwelling urinary catheter or conduit leading from the catheter. Embodiments of the apparatus comprise a dispenser configured to dispense inert or reactive matter into the urine stream to aid in the analysis of properties of the urine and an illumination device configured to illuminate the urine stream. Also described is a system comprising at least one of these apparatuses and at least one image analyzer unit operatively connected to it. The image analyzer unit comprises a processor and software adapted to analyze the captured images to derive information therefrom relating to identification of properties of the urine and/or objects of (Continued)

interest in the urine stream. Embodiments of the system may comprise other peripheral devices.

10 Claims, 6 Drawing Sheets

(51) Int. Cl.

| | | |
|---|---|---|
| *A61B 5/1495* | (2006.01) | |
| *A61B 5/145* | (2006.01) | |
| *G01N 33/493* | (2006.01) | |
| *A61B 5/00* | (2006.01) | |
| *A61B 5/20* | (2006.01) | |

(52) U.S. Cl.
CPC .......... *A61B 5/14507* (2013.01); *A61B 5/208* (2013.01); *A61B 10/007* (2013.01); *G01N 33/493* (2013.01); *A61B 5/6852* (2013.01)

(56) References Cited

U.S. PATENT DOCUMENTS

| | | | |
|---|---|---|---|
| 5,073,500 A | 12/1991 | Saito et al. | |
| 5,436,717 A * | 7/1995 | Ogino | ................ G01N 15/1404 250/458.1 |
| 5,561,517 A * | 10/1996 | Horiuchi | ................ G01N 15/14 356/39 |
| 6,384,915 B1 * | 5/2002 | Everett | ................ A61B 5/0066 356/336 |
| 2003/0010396 A1 | 1/2003 | Jurisch et al. | |
| 2006/0100743 A1 | 5/2006 | Townsend et al. | |
| 2009/0149776 A1 | 6/2009 | Adams | |
| 2010/0286559 A1 | 11/2010 | Paz et al. | |
| 2014/0306122 A1 * | 10/2014 | Norton | ................... G01N 15/14 250/428 |
| 2014/0329265 A1 | 11/2014 | Wanders et al. | |

FOREIGN PATENT DOCUMENTS

| | | |
|---|---|---|
| DE | 10221823 A1 | 11/2003 |
| DE | 10221823 B4 | 1/2006 |
| JP | H01178866 A | 7/1989 |
| JP | H01207662 A | 8/1989 |
| JP | H04194132 A | 7/1992 |
| JP | H07083818 A | 7/1995 |
| JP | 2010530056 A | 9/2010 |
| JP | 2007271331 A | 10/2017 |
| WO | 199920983 A3 | 8/1999 |
| WO | WO-2009142508 A1 * | 11/2009 ............. A61B 5/208 |

OTHER PUBLICATIONS

Nephrology in 30 Days, by Robert F. Reilly and Mark A. Perazella, McGraw-Hill, 2014. p. 220.

International Preliminary Report on Patentability in Corresponding PCT Application No. PCT/IL2015/051237 dated Jun. 21, 2017. 5 pages.

International Search Report in Corresponding PCT Application No. PCT/IL2015/051237 dated Mar. 27, 2016. 3 pages.

* cited by examiner

APPARATUS, SYSTEM, AND METHODS FOR URINALYSIS

CROSS-REFERENCE TO RELATED PATENT APPLICATIONS

This application is a U.S. National Phase Application under 35 U.S.C. § 371 of International Patent Application No. PCT/IL2015/051237, filed Dec. 21, 2015, and claims the benefit of priority under 35 U.S.C. Section 119(e) of U.S. Application Ser. No. 62/095,115, filed Dec. 22, 2014, all of which are incorporated by reference in their entireties. The International Application was published on Jun. 30, 2016 as International Publication No. WO 2016/103256 A1.

FIELD OF THE INVENTION

The present invention is from the field of medical devices. Specifically the invention relates to apparatus and methods for urine analysis, and more specifically to methods and apparatus for inline urine analysis

BACKGROUND OF THE INVENTION

Approximately 30% or more of intensive care patients contract some level of acute kidney injury (AM) during hospitalization. In many cases this leads to renal failure and necessitates some form of renal replacement therapy, such as dialysis or kidney transplant.

Dialysis reduces the quality of life of both the AKI patient and his/her family members. AKI also introduces a significant financial burden on a medical system/insurance system, including hospital beds taken for treatment, length of hospitalization of AKI patients having other treatments and the cost of the treatment itself. Dialysis also incurs significant risks to the patient, such as infection and even death.

Some reasons for the high levels of AKI in intensive care patients are the long response times of doctors, failure to diagnose in time, and poor and inaccurate methodologies currently available to estimate glomerular filtration rate and urine output over time as well as lengthy time to obtain the results of urinalysis for urine drawn from the patient.

Urinalysis, through microscopic and chemical examination of a sample of urine, can detect a number of features that are indicative of patient health. For example the concentration of various salts in the urine, the presence or absence of various substances (such as nitrites, sodium, potassium, calcium, phosphates) and bodies (such as WBC, RBC, epithelial cells, malignant cells, casts, crystals), the pH level, etc. are all important in determining the health of the patient.

Urinalysis is a standard procedure performed at health facilities around the world and typically consists of three parts:

1) Visual examination of properties such as color, clarity, concentration, turbidity.
2) Chemical tests, typically performed by inserting a prepared test strip (e.g., dipstick) into the urine. Chemicals are impregnated into the test strips and these react with the urine, changing color. Common tests include those for pH, protein, urea, glucose and creatinine.
3) Microscopic examination of the urine, typically the sediment remaining after centrifuging the sample. Many substances can be detected microscopically, such as cells, crystals, microorganisms, and casts.

The results of timely urinalysis can be critical in patient care. For example, with regard to detection of casts—"Red blood cell casts are indicative of glomerulonephritis or vasculitis; even one cast is very significant." (From: *Nephrology in 30 Days*, by R. F. Reilly & Mark A. Perazella, McGraw-Hill (2005), pg. 220). Urinalysis must be carried out on a urine sample within two hours of its collection.

An extensive literature of urinalysis exists, including many texts dedicated to the subject. A comprehensive review of the subject appeared in *American Family Physician* (Jeff A. Simerville, M. D., William C. Maxted, M. D., and John J. Pahira, M. D., Urinalysis: A Comprehensive Review, Am Fam Physician. 2005 Mar. 15; 71(6):1153-1162).

Unfortunately, despite the importance of urinalysis, prior art methods are labor-intensive, time-sensitive and time consuming, which, to date prevent its effective application.

Some patent publications in the art include US2006/0100743A, which describes a real-time, non-invasive system and method for determining the level of an analyte of interest in the urine of a patient. The system and method uses the measured level of an analyte of interest to detect the onset of acute renal failure (ARF) as early as possible to prevent that patient from developing the disease or to mitigate the effects of the disease. The system and method may be used to monitor the recovery of a patient after an ARF diagnosis. Preferably, the analyte of interest is creatinine or urea. The system may be placed in the urine drain line of a patient between a Foley catheter or other urinary drain and a urine collection bag. The system makes substantially continuous measurements of the urine flow rate and the concentration of the analyte of interest to determine the mass excretion rate of the analyte so it may be monitored to detect if the patient experiences a delta change in the mass excretion rate of an analyte that is indicative of the onset of ARF or a change in renal function. The method taught therein for determination of an analyte is the use of Raman spectrometry, tuned to the determination of a specific analyte.

US2010/0286559A describes a diagnostic method and apparatus for detecting at least one change in a urinary parameter indicative of a body malfunction, the method comprising at least semi-continuously monitoring in real time at least one of a sodium level, an oxygen level, a potassium level, and combinations thereof in the urine of a catheterized patient; whereby at least one parameter is monitored so as to detect one or more changes in the at least one parameter to reflect at least one of a fluid state, an electrolyte balance, a kidney state, a kidney perfusion and an organ perfusion in the patient, indicative of the body malfunction in the patient, in which the monitoring is preferably performed through electrodes that are arranged perpendicularly to the flow of urine through a patient's catheter system.

In these teachings, the determination of features of interest are limited to a small fraction of those available in a comprehensive analysis of the flow and constituents of urine, such as are determined in an offline urinalysis in a laboratory.

There thus remains an unmet need for improved systems and methods for comprehensive, real-time analysis of urine as it is being excreted in order to detect, diagnose and predict kidney failure and injury and other aspects of patient health.

It is therefore a purpose of the present invention to provide an apparatus and system for carrying out real-time inline urinalysis.

It is another purpose of the invention to provide an apparatus and system that provides real-time information about the urine flow rate.

It is another purpose of the present invention to provide improved systems and methods for diagnosing and predicting kidney failure and injury as well as other medical conditions that can be determined from urinalysis.

Further purposes and advantages of this invention will appear as the description proceeds.

SUMMARY OF THE INVENTION

In a first aspect the invention is an apparatus for inline urine analysis comprising:
a. at least one image capture unit comprising an image sensor and an optical assembly and
b. a control unit operatively connected to all other components of the apparatus by means of a wired or wireless communication channel. The control unit is configured to function as an input device that allows manual control, relay of control instructions from peripheral devices or programming of software and processing means in the control unit for automatic control of the image capture unit and any other components of the apparatus and also to function as an output device configured to transfer data related to the images gathered by the image capture unit data via wired or non-wired communication channel to peripheral devices.

The apparatus is configured to be coupled with an indwelling urinary catheter inserted into a patient's bladder or the conduit or tubing that leads from the catheter to a urine collection container or disposal system.

Embodiments of the apparatus of the invention comprise one or more of each of at least one of the following:
a. a dispenser configured to dispense different types of matter into the urine stream flowing through the catheter or conduit to aid in the analysis of properties of the urine; and
b. an illumination device configured to be able to illuminate the urine stream flowing through the catheter or conduit In embodiments of the apparatus of the invention the illumination devices are configured to illuminate the urine stream through at least one window in the catheter or conduit such that light reflected from or transmitted through the urine stream passes through the same or different windows in the catheter or conduit to be focused by the optical assembly onto the image sensor.

In embodiments of the apparatus of the invention at least one component of the apparatus is molded or assembled into the wall of a section of the catheter or conduit In embodiments of the apparatus of the invention at least one component of the apparatus is attached to a probe that is inserted into the catheter or conduit.

In embodiments of the apparatus of the invention the matter dispensed by the dispenser is one or more of: powders, particles, liquids, and gases (e.g., bubbles), microparticles, microspheres made of polystyrene or other materials, nano-particles, nano-spheres, and nanotubes.

In embodiments of the apparatus of the invention the matter dispensed by the dispenser comprises one or more of: chemical dyes or reagents injected directly into the urine stream or coated on or embedded in micro-particles, microspheres, nano-particles, nano-spheres, and nanotubes. These embodiments may comprise means for warming or cooling the urine to affect the rate of chemical reactions.

In embodiments of the apparatus of the invention the image capture unit comprises one of the following:
a. two polarizing filters to provide data that aids identification of crystals and lipids in the urine;
b. a condenser lens, a waveplate and a neutral density filter to perform contrast phase microscopy to produce data that can be used to identify and analyze cells in the urine;
c. one or more prisms and/or a diffraction grating to produce spectroscopic data that can be used to determine the identity and/or concentration of the constituents of the urine;
d. two polarizers and a microscope imaging system to provide data that can be used to perform optical mineralogy analysis to identify and analyze crystals in the urine;
e. a diverging lens to provide images that can be used to perform conoscopic analysis to identify and analyze crystals in the urine;
f. an illumination device that emits light of a specific wavelength or wavelengths to cause the urine or objects therein to emit light of a different wavelength and an optical assembly comprising a microscope imaging system that provides data that is used to perform fluorescence microscopy to identify and analyze organic and inorganic matter in the urine;
g. optical components configured to perform OCT (Optical Coherence Tomography) to provide data that is used to obtain high-resolution, 3D, images of the particles in the urine.

Embodiments of the apparatus of the invention comprise at least two image capture units configured in at least of the following ways:
a. one or more pairs of image capture units configured to yield stereo image pairs; and
b. image capture units placed at the same longitudinal position along the conduit but at different angles in a plane perpendicular to the axis of the conduit.

In a second aspect the invention is a system comprising at least one apparatus of the first aspect and at least one image analyzer unit operatively connected to the image capture unit and/or control unit through a wired or wireless communication channel the image analyzer unit comprising a processor and software adapted to analyze the images captured by the image capture unit to derive information therefrom relating to identification of properties of the urine and/or objects of interest in the urine stream.

Embodiments of the system of the invention comprise at least one of the following peripheral devices: a standard computer screen, a graphical user interface, a touch screen, a keyboard, a keypad, a touch pad, a stylus, alarm lights, auditory output, a storage system and media; a remote server, an alarm system, a portable communication device, a medical treatment device.

In embodiments of the system of the invention a single physical and/or logical unit may incorporate one or more dispenser units, image capture units, control units and an image analyzer unit or any subset of them.

In embodiments of the system of the invention a medical practitioner or software in the image analyzer or a peripheral computer analyzes the properties of the urine and/or objects of interest in the urine stream to determine medical conditions.

In embodiments of the system of the invention the image analyzer comprises software algorithms to enable one or more of the following machine vision techniques: pattern recognition, edge detection, filtering, color analysis, pixel counting, segmentation, and metrology.

In embodiments of the system of the invention the processor and software algorithms of the image analyzer are adapted to compare a plurality of images captured either from one image capture unit at different times or from two or more image capture units at the same or different times; thereby enabling the image analyzer to track the progress of one or more specific objects over time as they progress across the fields of view of the image capture units; thereby providing data that can be used by other software algorithms to calculate the progress, speed, and velocity of the specific objects through the conduit.

In embodiments of the system of the invention the processor and software algorithms of the image analyzer are adapted to use information about the physical properties of the conduit and the speed and/or velocity of specific objects through the conduit to calculate the volumetric flow rate of the urine through the conduit. In these embodiments a medical practitioner or software in the image analyzer or a peripheral computer may analyze the volumetric flow rate of the urine through the conduit to determine medical conditions.

In embodiments of the system of the invention the control unit controls the selection and timing of release of matter by the dispenser unit and makes the timing information available to the image analyzer unit, which is able to execute a software algorithm adapted to use the distance between the dispenser unit and the image capture unit and comparison of the time of release of said matter to the time of detection by the image capture unit to calculate the rate of travel of the matter in the catheter or conduit. In these embodiments the processor and software algorithms of the image analyzer may be adapted to use information about the physical properties of the conduit and the rate of travel of the matter through the conduit to calculate the volumetric flow rate of the urine through the conduit; and a medical practitioner or software in the image analyzer or a peripheral computer may analyze the volumetric flow rate of the urine through the conduit to determine medical conditions.

In embodiments of the system of the invention the processor and software algorithms of the image analyzer are adapted to detect chemical reactions. In these embodiments a medical practitioner or software in the image analyzer or a peripheral computer may analyze the chemical reactions to determine medical conditions.

In embodiments of the system of the invention at least one component of the system is disposable.

In a third aspect the invention is a section of an indwelling urinary catheter that is adapted to be inserted into a patient's bladder or of the conduit or tubing that leads from the catheter to a urine collection container or disposal system the section comprising at least one component of the apparatus of claim 1 molded or assembled into the wall of the section.

In a fourth aspect the invention is a probe configured to be inserted into an indwelling urinary catheter that is adapted to be inserted into a patient's bladder or into the conduit or tubing that leads from the catheter to a urine collection container or disposal system, wherein at least one component of the apparatus of claim 1 is attached to the probe.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

As used in this description, the term "image capture unit" refers to an apparatus comprising an image sensor and an optical assembly, which comprises at least an objective lens or lens system and may comprise additional optical elements, such as lenses, prisms, optical filters, mirrors, beam splitters, diffusers, apertures, irises, waveplates, and gratings. In embodiments of the invention in which images cannot be captured using only ambient light an illumination device is included in the image capture unit. In some embodiments of the invention the illumination device also comprises an optical assembly. The term "image sensor" refers to a device that converts light into electrical signals, for example a CCD or a CMOS sensor and electronics to output electrical signals corresponding to the images captured by the image capture unit. The term "image analyzer" refers to a processor configured to receive and analyze the electrical signals produced by at least one image sensor in order to produce a result. Such analysis may employ, inter alia, algorithms known in the art as machine vision or computer vision algorithms.

Figure 1:
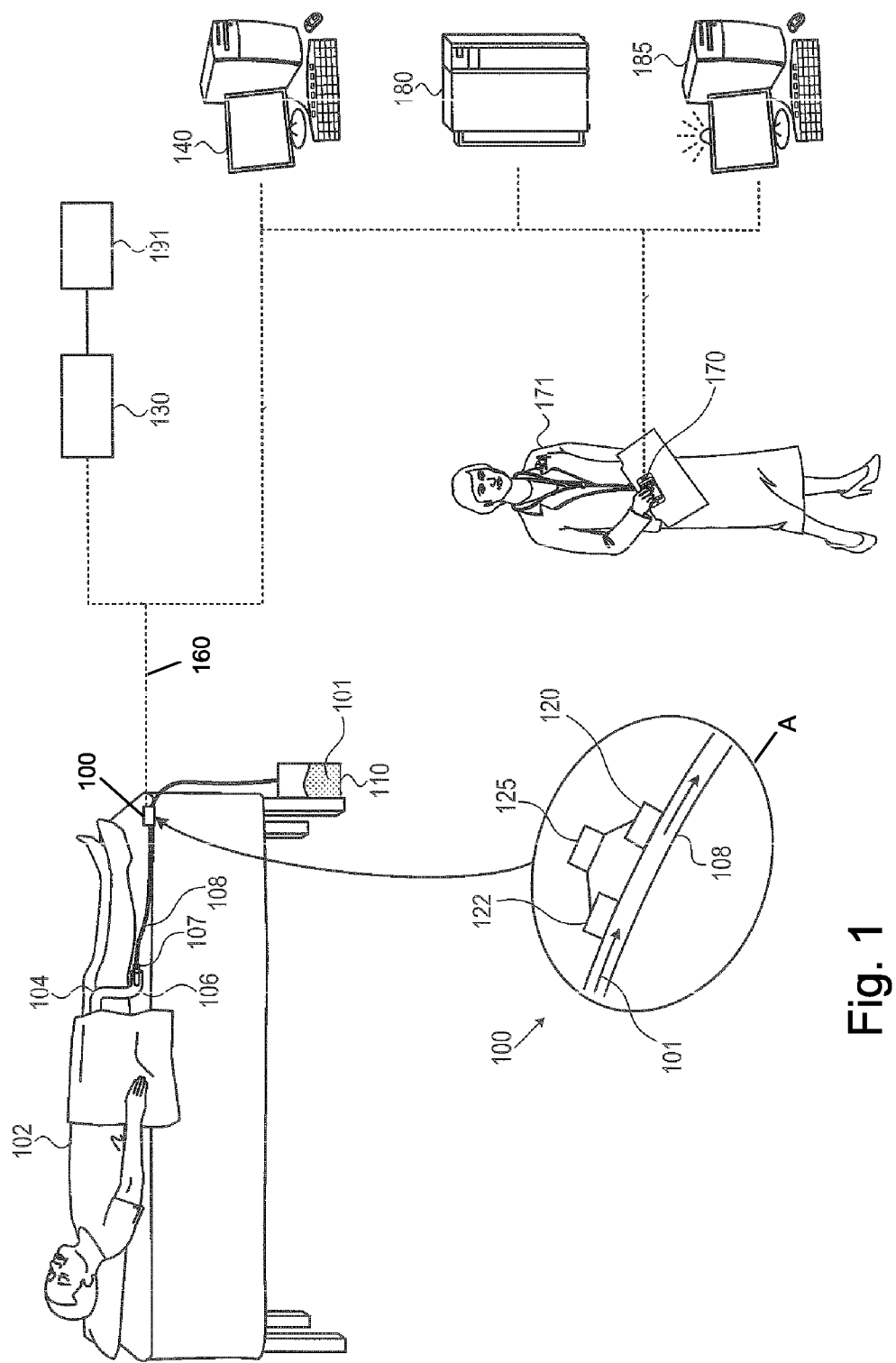
FIG. 1 schematically shows a system for inline urine analysis, in accordance with an embodiment of the present invention.

Reference is now made to FIG. 1, which is a simplified pictorial illustration showing a system for inline urine analysis, in accordance with an embodiment of the present invention. The system comprises at least apparatus 100, which comprises an image capture unit 120 and a control unit 125. Embodiments of the apparatus 100 may also comprise at least one of a dispenser 122 and illumination device in the image capture unit (see FIG. 2). The control unit 125 is operatively connected to all other components of apparatus 100 by means of a wired or wireless communication channel and may be operatively connected through a wired or wireless communication channel 160 to other peripheral device(s) in the system, such as an image analyzer 130, as described below.

The apparatus 100 of the present invention is adapted for inline use without pre-centrifugation of the urine. The embodiments of apparatus 100 and the systems in which it is deployed are constructed and configured to identify objects in the urine and use analysis techniques to determine concentrations of these objects from continuous urine flow that are equivalent to those achieved through centrifugation. The purpose of centrifugation of the urine is to simplify manual microscopic examination, whereby the sediment contains the endogenous bodies of interest and are examined under a microscope in a concentrated form. Since apparatus 100 can be configured to continuously capture images from the urine stream, it is not necessary to concentrate the bodies in order to capture and analyze them. Whenever an endogenous body passes through the field of view of the image capture unit, it will be captured for analysis. In other words, the analysis "virtually concentrates" the urine constituents without the need to physically do so.

A patient 102, such as an intensive care unit (ICU) patient, is catheterized with an indwelling urinary catheter 104, such as a Foley catheter. The catheter is typically inserted into the patient's bladder (not shown) and anchored with an inflatable balloon within the bladder. At the other end of the catheter is a connector 106 (e.g., a luer-slip connector). The connector 106 connects to a mating connector 107 of a conduit or tubing 108 that leads to a urine collection container 110. Urine 101 passes from the patient via the catheter, connectors and conduit to the collection container 110. An apparatus of the invention 100 is attached, for example by means of clamps that clamp onto the catheter 104 or tubing 108 at some location along the line from patient 102 to collection container 110 in such a fashion as to be able to capture images of the urine stream within the catheter or conduit. An embodiment of the apparatus comes pre-attached to a short section of conduit with connectors at both ends to allow it to be inserted between connectors 106 and 107. In another embodiment, a section of the conduit or catheter is passed through a mating channel of a housing comprising the apparatus of the invention configured to capture, through the wall of the conduit, images of the urine flowing through the conduit. In another embodiment a section of the conduit or catheter is specially formed to facilitate insertion into the housing. The specially formed section may incorporate some or all of the optical elements of the image capture unit built into the wall of the section (for example, a clear, molded conduit incorporating a molded lens). In another embodiment, the conduit or catheter may incorporate part or all of the apparatus (for example the image capture unit and a dispenser may be molded or assembled into the wall of a section of the catheter or conduit). In an embodiment, part or all of the apparatus may be incorporated into a probe that is inserted into the interior of the conduit or catheter.

Inset "A" in FIG. 1 schematically shows an embodiment of the apparatus 100 of the invention. The embodiment of the system shown in this figure comprises a dispenser unit 122 that is provided to dispense different types of matter into the conduit to aid in the analysis of the properties of the urine. As shown, apparatus 100, including the dispenser unit 122 is attached to conduit 108 with the dispenser unit 122 upstream (arrow 101 shows the direction of urine flow) and the objective lens of image capture unit 120 focused on the urine flowing through the conduit.

The control unit 125 functions as an input device to control the dispenser unit 122 and the image capture unit 120. When functioning as an input device control unit 125 allows manual control, relay of control instructions from peripheral devices, and/or programming of software and processing means in the control unit for automatic control. Control unit 125 also functions as an output device that is able to transfer data related to the images gathered by the image capture unit via a wired or non-wired communication channel 160 to an external unit such as an image analyzer unit 130 that comprises a processor and software to analyze the images as described below.

The control unit 125, image capture unit 120, dispenser unit 122, and image analyzer unit 130 are described in further detail herein below with respect to FIGS. 2 and 3.

One or both of the apparatus 100 and the image analyzer unit 130 may be operatively connected to other device(s), computer(s) or system(s) via one or two-way communication channels 160, which can be for example a network such as a LAN, VPN, and the Internet; an intermittent communication link; a wired link; a wireless link; a mobile data link, such as a cellular network; and means for transferring data on a physical medium.

Examples of devices, computers or systems that can be connected to the apparatus 100 of the invention include (but are not limited to): a remote server 180, an additional analysis or storage system 140, an alarm system 185, a portable communication device 170 such as a tablet computer or cell phone or any external system (not shown), such as a treatment device, for example, an infusion pump.

One or more of the image capture unit 120, the image analyzer unit 130, control unit 125, and any operatively connected device, computer, and system may be constructed and configured to transmit and/or receive raw and/or processed data. The data transmitted and/or received may include, inter alia, patient data, urine flow data, urine chemical data, raw images, processed images, image metadata, results of analysis (whether intermediate or final) or other data related to urine properties or other data. Each of the types of data may be transmitted independently or in arbitrary combinations.

The system may further comprise an alarm 191, adapted to provide a signal, such as a light and/or audible signal and/or mechanical signal such as vibration and/or text message and/or other signal upon activation by apparatus 100 or any component of the system.

In embodiments of the invention one or both of the image analyzer unit 130, and the control unit 125 is optionally operative to update a health service provider, such as a nurse or doctor 171 via any device, such as a portable communication device 170, for example a cell phone or tablet computer, a portable computer, an intercom, beeper, and a non-portable device such as a desktop computer.

In some embodiments the image analyzer unit 130 and control unit 125 may be separate units as shown in FIG. 1; and, in other embodiments, they may be provided as a single unit, for example as a dedicated computer, a standard computer, laptop computer, or tablet computer comprising dedicated and other software for operating the system and analyzing the images, and as an application on a smartphone. If provided either as separate units or as a combined unit the image analyzer unit 130 and control unit 125 in different embodiments further comprise or are connected to one or more peripheral devices, such as a display, e.g. a standard computer screen, a graphical user interface, and a touch screen; an input device, e.g. a keyboard, keypad, touch pad, or stylus; lights, auditory output, and storage media for storing, inter alia, the data received from the image capture unit and the results of analysis or other processing.

As described above for the case of the image analyzer unit 130 and the control unit 125, in various embodiments the functions or structure of the dispenser unit 122, image capture unit 120, image analyzer unit 130, and control unit 125 may be provided as separate components or combined or integrated in various configurations involving one, two, three or all four of the components. For example, a single physical and/or logical unit may incorporate all four components or any subset of them. Additionally or alternatively, in some embodiments, the components may be operatively connected in more complex configurations. For example, one image analyzer may be operatively connected to a plurality of image capture units, and one image capture unit may be operatively connected to a plurality of image analyzers, or both, and one control unit may control a plurality of image capture units and/or dispensers and be connected to a plurality of image analyzers.

Figure 2:
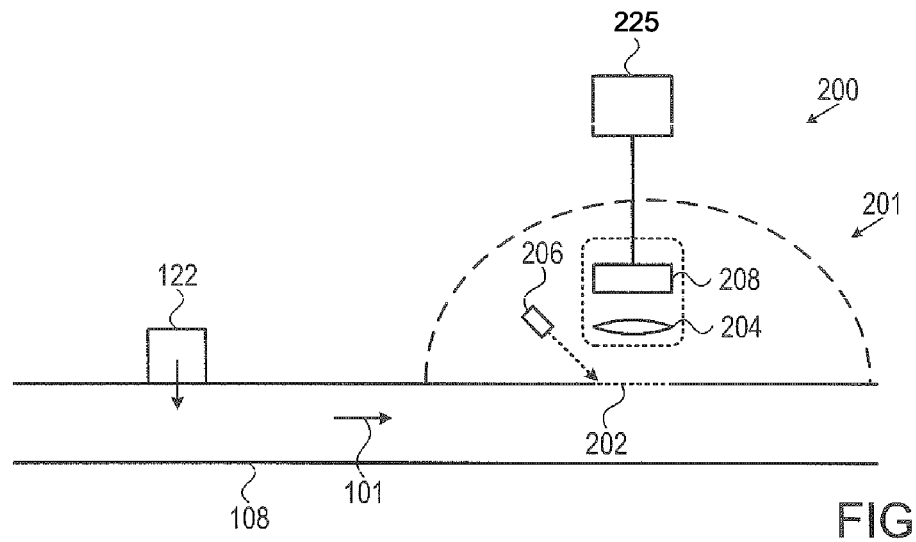
FIG. 2 schematically shows an apparatus for inline urine analysis, in accordance with an embodiment of the present invention.

Reference is now made to FIG. 2, which schematically shows another embodiment of the apparatus of the invention, for inline urine analysis. In the embodiment shown apparatus 200 comprises dispenser 122 upstream of an image capture unit 201 located on conduit or tubing 108. Urine 101 passes through conduit 108 from the patient to the region of the dispenser unit 122 and continues to the region of the image capture unit 201. The arrow 101 indicates a direction of ordinary flow, although flow may temporarily be stopped or reversed. The conduit has one or more transparent windows 202. In the embodiment shown the image capture unit is constructed and configured to be able to illuminate the urine stream in the conduit via window 202 by means of an illumination device 206, comprising, for example one or more LEDs; a laser; or another type of light source such as incandescent or fluorescent lamp. Ambient lighting may be used to illuminate the urine together with the other source in this embodiment. In other embodiments that do not include an illumination device 206 ambient lighting alone might be sufficient. In some embodiments there are several illumination sources that emit light of the same or of different types (e.g., polarized, collimated, ultraviolet (UV), infrared (IR), near-infrared (NIR), and visible, including different wavelengths) and/or for different purposes.

The image capture unit comprises an optical assembly 204, constructed and configured to receive light either through the same window that the illumination device 206 illuminates the urine stream or through a different window. In the arrangement shown in FIG. 2, the optical assembly focuses light reflected from the urine stream onto the image sensor 208. In another arrangement there can be a second window on the side of the conduit opposite to window 202, the light source 206 can then be arranged to illuminate the urine stream through the second window and optical assembly 204 will focus light transmitted through the urine stream onto the image sensor 208. In some embodiments, both reflected and transmitted light are used. According to some embodiments, optical assembly 204 comprises a microscope imaging system to provide magnified images of the urine stream. In some embodiments, part or all of the optical assembly 204 is incorporated into the window 202. In some embodiments part or all of the components of image capture unit is attached to a probe that is inserted into the catheter or conduit.

Image analyzer unit 130 (see FIG. 1) receives electrical signals from the image capture unit 208 via control unit 225 and analyzes the signals to derive information therefrom. Image analyzer unit 130 comprises a processor and software comprising algorithms to enable inter alia the analysis to include techniques known in the art of machine vision, including, but not limited to, pattern recognition, edge detection, filtering, color analysis, pixel counting, segmentation, and metrology. The object of such analysis is to identify properties and/or objects of interest in the urine stream, for example, color, clarity/turbidity, white blood cells, red blood cells, crystals, casts and other objects that may be present in the urine stream.

In some embodiments, processor and software in the image analyzer unit 130 comprise algorithms that allow comparison of a plurality of images captured either from one image capture unit at different times or from two or more image capture units at the same or different times. By so doing, the image analyzer 130 is able to track the progress of one or more specific objects over time as they progress across the field of view of the image capture units, thereby providing data that can be used by other algorithms to calculate their progress, speed, and velocity through the conduit. Using information about the physical properties of the conduit, such as its cross-section, the image analyzer algorithms may further determine the urine volumetric flow rate through the conduit, which reflects the rate of urine excretion by the patient. Urine excretion or output rate is a parameter of clinical interest in determining the health of the patient, including eGFR and risk of AKI.

The dispenser unit 122 is constructed to dispense different types of matter into the conduit. The matter dispensed may be chemically inert, chemically reactive, or a combination thereof. For example, dispenser unit 122 may dispense matter provided in many forms, for example, as powders, particles, liquids, and gases (e.g., bubbles), and objects such as: micro-particles, microspheres made of polystyrene or other materials, nano-particles, nano-spheres, and nano-tubes. These may be combined with other substances, e.g., impregnated, embedded, and/or coated using many methods known in the art, such as, but not limited to, covalent binding or adsorption.

For urine that is very dilute and thus contains a comparatively low number of endogenous bodies, exogenous matter dispensed by the dispenser is used to calculate flow rates as described above, using the travel time of the matter across the field of view of the image capture unit. Exogenous matter introduced by the dispenser has dimensions small enough to not get trapped in the urine conduit and has buoyancy so as not to rise to the top nor sink to the bottom of the urine.

In some embodiments the control unit 125 controls the selection and timing of release of matter by the dispenser unit 122 and makes the timing information available to the image analyzer unit 130, which is able to execute a software algorithm that uses this information to calculate the rate of flow by knowing the distance between the dispenser unit 122 and the image capture unit 120 and comparing the time of release of said matter to the time of detection by the image capture unit 120.

In some embodiments, the dispenser unit 122 dispenses matter that is chemically inert and in some embodiments matter that is chemically reactive and in some embodiments combinations thereof. The dispenser may dispense one type of matter or a plurality of types or a selection from a plurality of types.

When dispensing matter that is chemically reactive, the distance between the location at which the dispenser unit 122 introduces the matter into the urine stream and the upstream edge of window 202 is adjusted to allow for the expected chemical reaction time to elapse while the matter travels through the conduit to the image capture unit. The image analyzer unit 130 is then able to analyze the images to determine the result, if any, of the chemical reaction, such as change in color.

According to some embodiments of the present invention, the chemical analyses employed includes use of any of the chemical dyes that are presently used for urine dipsticks or test strips. These chemical dyes may, for example, be applied to the exterior of microspheres or other objects dispensed into the urine stream or injected directly into the urine stream in liquid, powder or other form.

Using suitable chemicals (reagents), appropriately treated matter is dispensed into the urine stream in order to facilitate detection of a variety of parameters. The reagents include any of the known urine test reagents; for example, a pH indicator, a protein indicator, an albumin indicator, a creatinine indicator, a uric acid indicator, a blood particle indicator, a bacterial indicator, a viral indicator, a fungal indicator, a parasite indicator, a ketone indicator, a glucose indicator, a nitrite indicator, a sodium indicator, a potassium indicator, a magnesium indicator, a kidney stone indicator, an oxalate indicator, a chloride indicator, a bilirubin indicator, a urobilinogen indicator, a specific gravity indicator, a glucose indicator, a leukocytes (white blood cells) indicator, an erythrocytes (red blood cells) indicator, a heme indicator, a hemoglobin indicator, a kidney disease indicator and a kidney injury indicator.

The reagents may be dispensed in gaseous, liquid or powder form or combined with other matter. For example, microspheres are commercially available coated with a variety of substances and nanotubes may be constructed with embedded substances. Exposure to light of the appropriate wavelength ruptures the nanotubes thus exposing the embedded substance to the urine potentially causing a chemical reaction to occur. In such a case an alternative or additional illumination source (not shown in the figures) to emit the rupturing light is included. Similarly, other matter may be introduced to the urine stream that contains chemically reactive reagents that cause a chemical reaction to occur, the results of which are identified by the system.

Some embodiments of the present invention incorporate a means for warming or cooling the urine to affect the rate of chemical reactions. For example, in an embodiment the illumination device 206 comprises an IR light source to warm the urine. Other examples of means to warm or cool the urine include, for example, resistive heating elements, Peltier elements, microwaves, radio frequency waves, and ultrasound.

In certain embodiments, the illumination device 206 and optical assembly 204 in the image capture unit 201 are designed to perform various additional types of optical analysis. For example, different wavelengths of light excite crystals to aid in their identification. Similarly, in some embodiments, the illumination device 206 is constructed and configured to enable the image capture unit 201 and/or image analyzer 130 to provide excitation and absorption data that aids in identification of urine constituents. Some embodiments of the invention use polarized light.

The use of polarized light is common in performing various analyses such as identifying crystals and lipids. Thus, for example, using a polarizing filter as part of the illumination device yields polarized light. An additional polarizing filter disposed in the optical assembly permits identification and analysis of birefringent substances in the urine, such as crystals, fatty casts, fat droplets, oval fat bodies, etc. As examples of the utility of polarized light, crystals display a characteristic color under these conditions and lipids display a Maltese cross formation. The polarizing filters may be static polarizers or switchable, i.e., devices that may allow all light to pass through or, when activated, allow only the light waves vibrating in a certain direction (i.e. polarized) to pass. A switchable polarizer may be constructed using techniques known in the art, such as with liquid crystals.

In embodiments phase contrast microscopy techniques are used. In these embodiments, the illumination device comprises a condenser lens and the optical assembly in the image capture unit comprises one or more phase shifting waveplates and one or more neutral density filters to create the phase contrast effect. The phase shift waveplates may be static or switchable or adjustable. A switchable or adjustable phase shift waveplate may be constructed using techniques known in the art, such as with liquid crystals. Phase contrast microscopy is useful in identifying cells in the urine.

In embodiments spectroscopic analysis techniques are used. In these embodiments the image capture unit comprises one or more prisms and/or a diffraction grating that produce a spectrum of reflected or transmitted light from the urine stream on the image sensor. Software in the image analyzer can analysis the spectrum to determine the identity and/or concentration of the constituents of the urine.

In embodiments optical mineralogy analysis is performed to identify and analyze crystals in the urine. In these embodiments the image capture unit comprises a polarizer between the illumination device and the urine stream and an optical assembly comprising a microscope imaging system and a second polarizer.

In embodiments conoscopic analysis is performed to identify and analyze crystals in the urine. In these embodiments the image capture unit comprises at least a diverging lens to transform the optical image into a directional image as known in the art of conoscopy. These embodiments may also include other optical elements to aid in imaging the interference figure, such as a polarizer between the illumination device and the urine stream and a second polarizer, an optical assembly comprising lenses, an adjustable aperture or diaphragm (such as an electronic iris), and a microscopic imaging system. An example of the application of this technique is to aid in distinguishing between $CaCO_3$ and $NaCl$ crystals, which may be of clinical interest. Similarly, other minerals of interest in urine may be identified and analyzed.

In embodiments of the image capture unit the illumination device emits light of a specific wavelength or wavelengths (such as ultraviolet) to cause the urine or objects therein to emit light of a different wavelength and the optical assembly comprises a microscope imaging system that provides data that is used to perform fluorescence microscopy to identify and analyze organic and inorganic matter in the urine.

Other embodiments of the image capture unit are configured to perform OCT (Optical Coherence Tomography)— for obtaining high-resolution, 3D, images of the particles in the urine, including penetration to a depth of 1-2 mm or other depth as may be appropriate and available in the art of OCT.

Embodiments of the invention comprise a plurality of image capture units. In various embodiments, the configuration of the plurality of image capture units yields different types of information. For example, a pair of image capture units may be configured to yield a stereo image pair thus providing additional information about the urine stream and its constituents. Image capture units placed at the same longitudinal position along the conduit but at different angles in a plane perpendicular to the axis of the conduit also provide additional information about an object carried in the urine stream. Other configurations comprising a plurality of image capture units are also possible to enhance the image analysis performed. These are described in greater detail with respect to FIG. 3A and FIG. 3B.

Figure 3A:
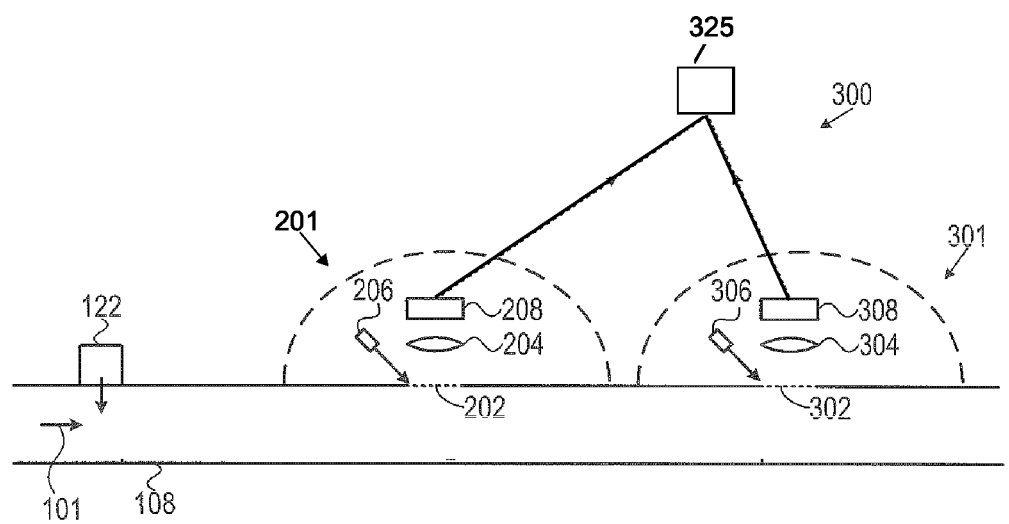
FIG. 3A is a simplified schematic illustration showing an apparatus for inline urine analysis, in accordance with an embodiment of the present invention.

Turning to FIG. 3A, there is seen another schematic illustration showing a system 300 for inline urine analysis, in accordance with an embodiment of the present invention.

In the embodiment shown in this figure, two image capture units 201,301 are shown with their respective illumination devices 206,306 illuminating the urine stream in conduit 108 and their respective optical assemblies focused through windows 202, 302. In some embodiments a single window may serve multiple image capture units. The images from the two image capture devices may be captured simultaneously for stereoscopic pair or other multiple-viewpoint analysis or at different times for example to measure the speed of an object moving with the stream of urine.

System 300 comprises an optional dispenser 122 upstream of the two image capture units 201, 301 on conduit or tubing 108. Urine flowing in the direction indicated by arrow 101 passes along the conduit from the region of the dispenser 122 to the region of the first image capture unit 201. The conduit has one or more transparent windows 202, 302. The image capture units 201, 301 are substantially similar, or identical, in composition comprising respectively optical assemblies 204, 304, and image sensors 208, 308. In this embodiment both image capture units 201, 301 are connected to a single control unit 325. The components of the system and the system as a whole function in the same way as described with respect to FIG. 2.

With the appropriate configuration of image capture units, stereo image pairs may be captured. Various means of 3D image processing may also be employed by image analyzer 130 including, for example, analysis of stereo image pairs, construction of a 3D model, and laser triangulation.

In another embodiment, the two image capture units are used by the image analyzer to track the time it takes for an object or a set of objects to travel the distance between corresponding locations in the fields of view of the two image sensors from which measurement of the corresponding urine flow rate is calculated.

In some embodiments, a plurality of dispensers 122 (not shown) release matter under the control of a control unit 125. The timing of the release is chosen to detect appropriate chemical reactions. By way of non-limiting example, the same matter may be dispensed at two different locations upstream of the image capture unit. A first set of matter is dispensed into the urine stream from the dispenser furthest upstream and when it arrives at the next dispenser, more matter is dispensed. Then the two sets of matter arrive together at the image capture unit. However the first batch has been in the urine longer than the second batch. Having been released at different locations and times the two sets of matter will represent different times of reaction. Various combinations and arrangements of dispensers and image capture units allow for a variety of situations and all such arrangements are within the scope of the present invention.

Figure 3B:
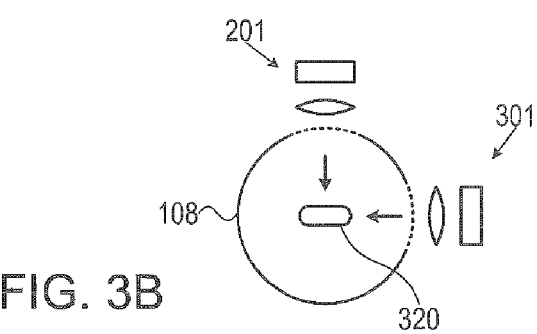
FIG. 3B is a simplified schematic illustration showing an apparatus for inline urine analysis, in accordance with an embodiment of the present invention.

Turning now to FIG. 3B, image capture unit 201 and image capture unit 301 are both disposed at the same longitudinal position along the conduit. Image capture unit 201 and image capture unit 301 are located at different angles around the circumference of the conduit in a plane perpendicular to the longitudinal axis of the conduit. In the illustrative figure, the angle is 90°, however any angle may be used as appropriate. For simplicity, not all components of the devices 201, 301 are shown in FIG. 3B.

When comparing images captured by the two image capture units 201, 301 at their respective angles, the image analyzer derives additional information about an object 320 viewed in the urine stream, including shape, position, orientation, depth, etc. Such information can be used to disambiguate an object captured in images—for example a red blood cell seen from the side can resemble a platelet.

In another embodiment, the configuration shown in FIG. 3B may be replicated at a distance downstream of a first such configuration and the image analyzer uses the information from the plurality of images to aid in identifying objects that may change their orientation as they travel the distance between the locations of the pairs of image capture units.

In the foregoing description configurations using pairs of image capture units have been described, but any number of devices may be used in any configuration.

Figure 4A:
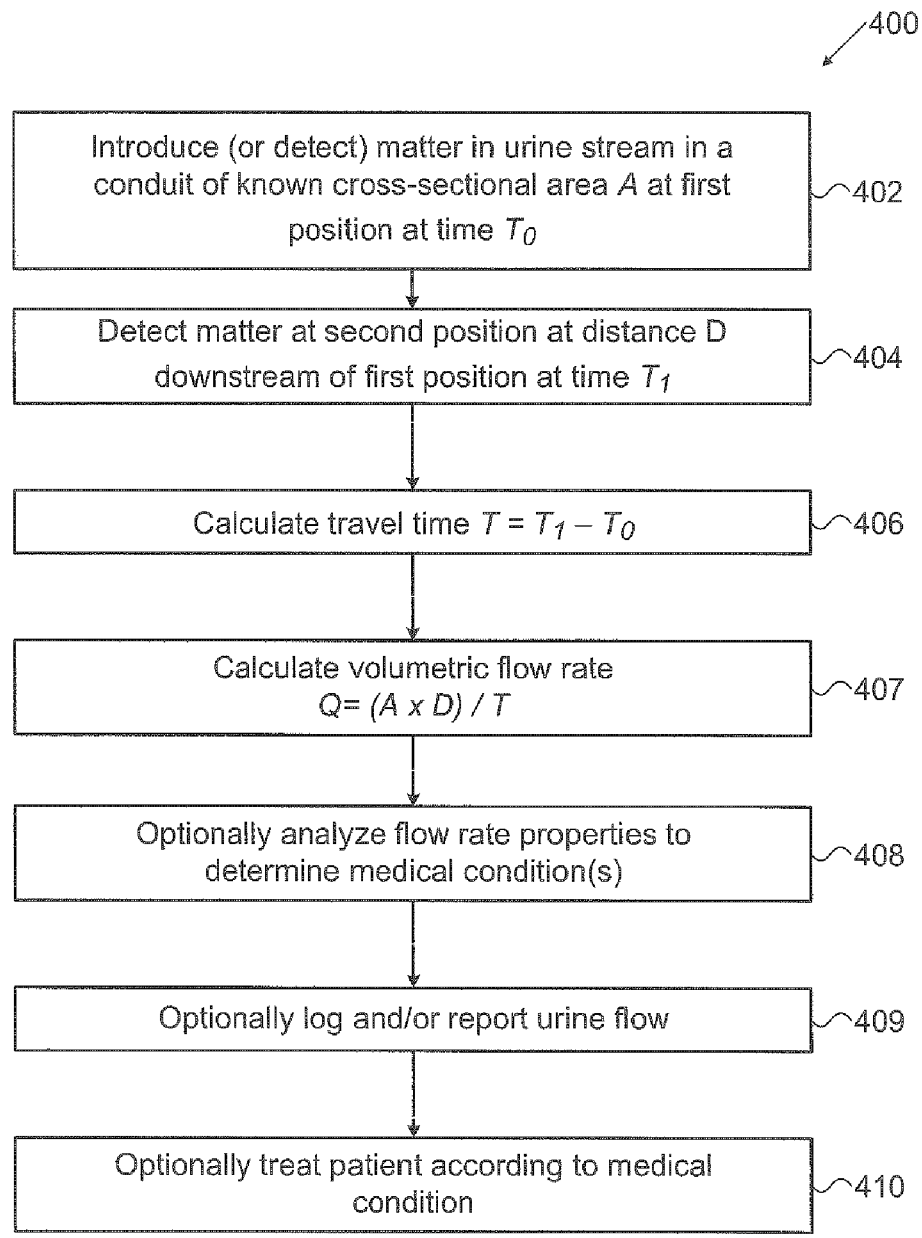
FIG. 4A is a simplified flowchart of a method for inline urine analysis and measurement, in accordance with an embodiment of the present invention.

Reference is now made to FIG. 4A, which is a simplified flowchart 400 of a method for inline urine analysis, in accordance with an embodiment of the present invention.

In step 402 the control unit sends instructions to the dispenser to dispense a certain quantity of at least one type of matter into a conduit of known cross-sectional area A at time $T_0$. According to some embodiments, the matter is selected from the group consisting of a color, a dye, a reactant, a reagent, an indicator, a biochemical and a particulate matter, such as microspheres, nanospheres, nanotubes, powder, etc. According to some embodiments, the matter includes inert matter or chemically reactive matter or combinations thereof. Alternatively or additionally, in step 402, an image capture unit and image analyzer are operative to detect previously introduced matter or endogenous matter or objects.

In step 404, at least one image capture device and software in the image analyzer are operative to detect at time $T_1$ matter introduced in step 402 or endogenous matter at one or more positions downstream of a first position.

Data produced in step 404, is analyzed by software in the image analyzer in step 406 to determine the velocity of urine flowing from the dispenser to a first image capture unit and/or to a second image capture unit (FIG. 3A, for example). In step 406, the travel time $T=T_1-T_0$ from a first position to a second position is calculated where the first position may be either that of a dispenser or an upstream image capture unit and the second position is a downstream image capture unit.

In step 407, the volumetric flow rate Q is calculated by software in the image analyzer based on the known distance D traveled over the calculated time T and the known cross-sectional area A of the conduit: $Q=(A \times D) \div T$.

Step 408 is an optional step in which the results of step 407 are further analyzed by a medical practitioner or software in the image analyzer or a peripheral computer to determine medical conditions such as kidney and urinary tract disorders. Such analysis may involve comparison to historical data for the same patient (e.g., to determine sudden changes in flow rate or to identify developing trends that may be indicative of medical conditions of clinical interest), or to a database of related values or to medical criteria as are of may be defined to indicate conditions of clinical interest (e.g., RIFLE, AKIN), or other types of analysis based on a urine property determined.

Step 409 is another optional step in which the data gathered in step 407 may be logged either locally in a data store in the control unit or analyzer or in a remote system. Additionally or alternatively, if the data is determined by a medical practitioner or software in the control unit, image analyzer or another peripheral computer, to be of clinical interest, for example, a sudden change in flow rate or a flow rate below or above a threshold, it may be logged, or reported to another system or person or other entity. Such reporting may be through any means, including electronic communication, display on a screen, alerting through visual, aural or mechanical means, e.g. displayed as text, sounding an alarm, activating a buzzer or vibrator, sending a text or voice message.

Step 410 is another optional step in which the patient is treated responsive to his/her urine flow rate determined by steps 402-408. For example, the patient may be provided with additional fluids, salts, vitamins, antioxidants, antibiotics, diuretics, anti-diuretics, medicaments and combinations thereof.

Figure 4B:
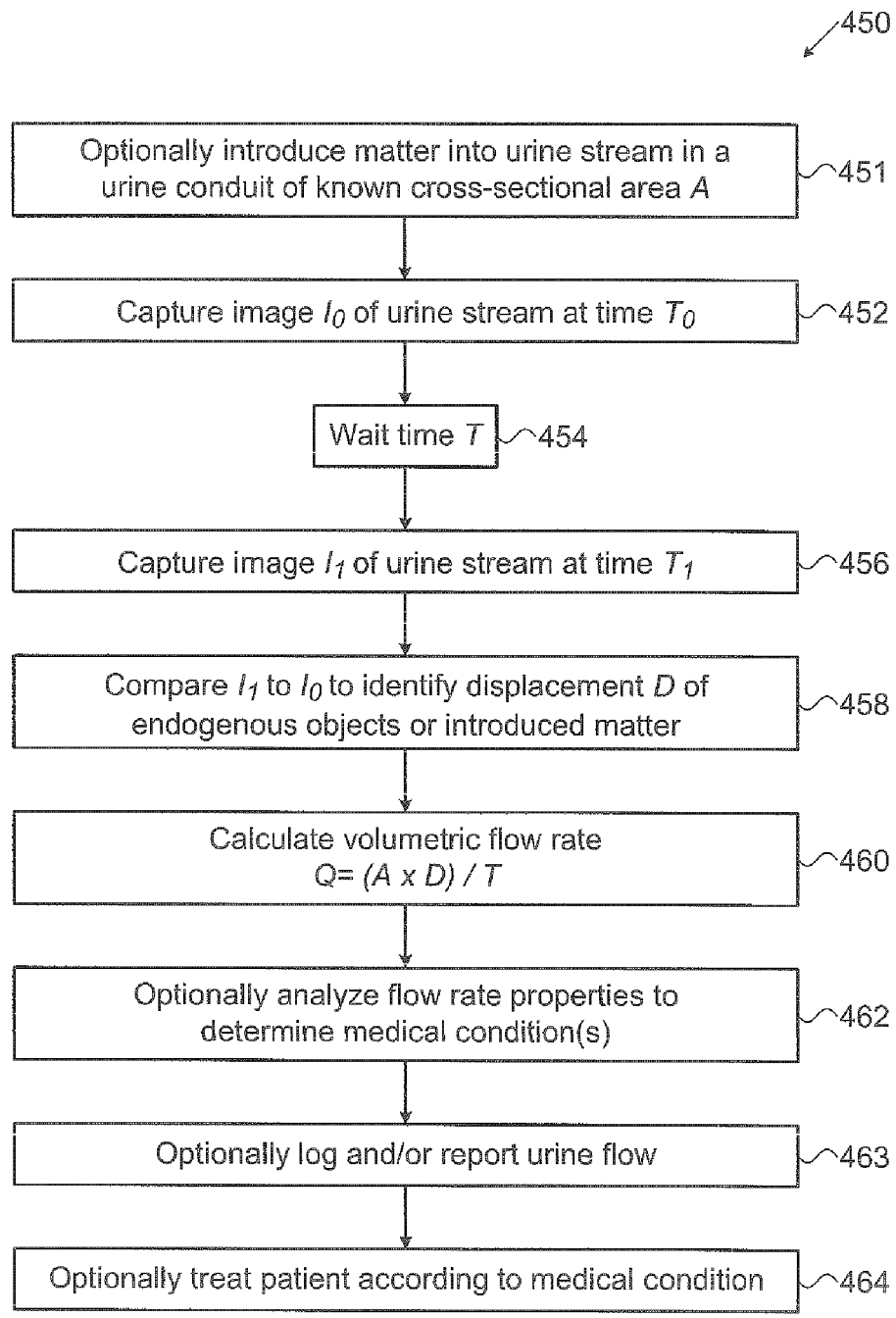
FIG. 4B is a simplified flowchart of a method for inline urine analysis and measurement, in accordance with an embodiment of the present invention.

Reference is now made to FIG. 4B, which is a simplified flowchart 450 of a method for inline urine analysis, in accordance with an embodiment of the present invention.

Step 451 is an optional step in which the control unit sends instructions to the dispenser to dispense a certain quantity of at least one type of matter into a conduit of known cross-sectional area A at time $T_0$.

In step 452, at least one image capture unit is operative to capture a first image $I_0$ of the urine stream at time $T_0$.

Step 454 comprises waiting for an interval of time T to pass.

In step 456 a second image $I_1$ is captured by the same or a different image capture unit.

In step 458, the images $I_1$ and $I_0$ are compared by software in the image analyzer or a peripheral computer to determine the distance (D) that objects within the urine stream have been displaced during time T.

In step 460 the volumetric flow rate of the urine $Q=(A \times D) \div T$ is calculated by the image analyzer, using, for example Particle Image Velocimetry (PIV) software or Laser Doppler velocimetry, depending on the illumination device and optical assembly used.

Step 462 is an optional step in which the results of step 460 are further analyzed by a medical practitioner or software in the image analyzer or a peripheral computer to determine medical conditions such as kidney and urinary tract disorders.

Step 463 is another optional step in which the data gathered in step 460 may be logged either locally in a data store in the control unit or analyzer or in a remote system. Additionally or alternatively, if the data is determined by a medical practitioner or software in the control unit, image analyzer or another peripheral computer, to be of clinical interest, for example, a sudden change in flow rate or a flow rate below or above a threshold, it may be logged, or reported to another system or person or other entity.

Step 464 is another optional step in which the patient is treated responsive to his/her urine flow rate determined by steps 451-460.

Figure 4C:
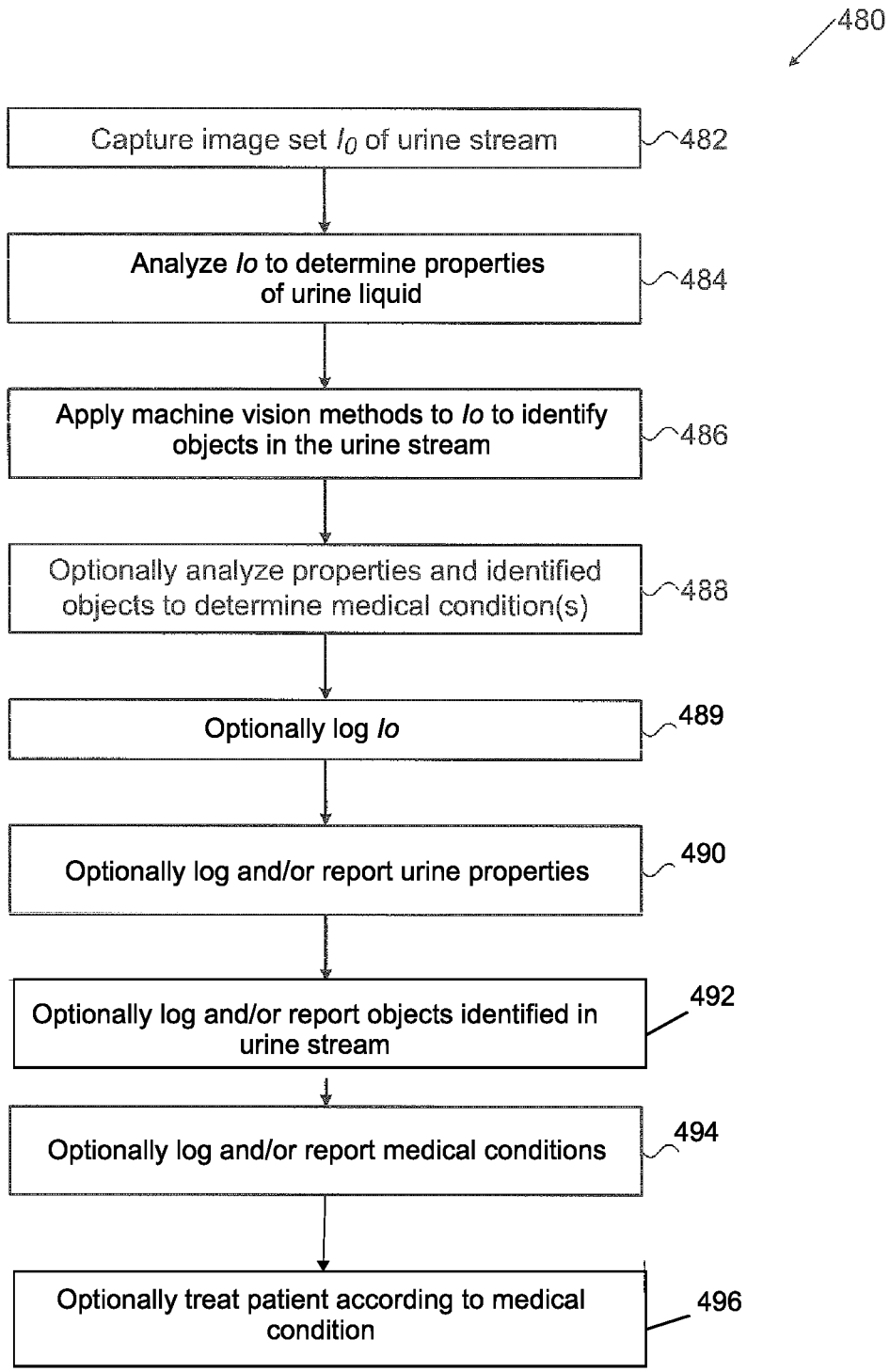
FIG. 4C is a simplified flowchart of a method for inline urine analysis and measurement, in accordance with an embodiment of the present invention.

Reference is now made to FIG. 4C, which is a simplified flowchart 480 of a method for inline urine analysis, in accordance with an embodiment of the present invention.

In step 482, the control unit sends instructions to at least one image capture unit to capture a first image set $I_0$ comprising at least one image of the urine stream and $I_0$ is logged in a database of the control unit or image analyzer.

In step 484, the image set is analyzed by software in the image analyzer to determine at least one property of the urine stream, such as color, clarity, and/or turbidity. Step 484 may be performed multiple times to determine different properties of the urine.

In step 486, machine vision software in the image analyzer is operative to identify through the use of machine vision algorithms various endogenous bodies and/or introduced objects in the urine stream. As described above, this step may include, for example, the use of multiple images from different angles or positions, such as for stereoscopic imaging or other types of visual analysis. In certain embodiments this step includes identification of urine constituents through the use of light of a particular wavelength and/or polarization and/or orientation, as described above. Examples of endogenous bodies that may be identified include cells, crystals (such as calcium oxalate, calcium phosphate, sodium urate, amorphous phosphate and ammonium magnesium phosphate, etc.), microorganisms, cells (such as red blood cells, white blood cells, renal tubular cells, etc.), casts (such as those made up of hyalines, granular, waxy bodies, fatty globules, red blood cells, white blood cells, renal tubular cells, etc.), and other bodies.

In embodiments of step 486 in which the apparatus includes appropriate optical elements in the optical assembly, such as a diffraction grating or one or more prisms, polarizers, or a microscope imaging system the image analyzer comprises software adapted to carry out spectroscopic analysis techniques, and/or to perform phase contrast microscopy and/or optical mineralogy analysis, and/or conoscopy to identify and/or analyze the crystals in the urine, and or to employ OCT to identify and/or analyze constituents of the urine. Step 484 may be performed multiple times to carry out some or all of these techniques.

Step 488 is an optional step in which the results of steps 484 and/or 486 are further analyzed by a medical practitioner or software in the image analyzer or a peripheral computer to determine medical conditions and/or potential medical conditions (e.g., proteinuria, blood in urine, cast(s) present, drugs present, urinary tract infection (UTI), AKI, other kidney or urinary tract disorders, liver conditions, bile duct conditions, etc.). Such analysis may involve comparison to historical data for the same patient (e.g., to determine sudden changes in urine properties or to identify developing trends that may be indicative of medical conditions of clinical interest), or to a database of related values or to medical criteria as are or may be defined to indicate conditions of clinical interest, or other types of analysis based on a urine property determined.

Steps, 489, 490, 492, 494, which comprise logging the data gathered in steps 482, 484, 486 and 488 respectively are optionally performed. The data gathered in steps 482, 484, 486 and/or 488 may be logged either locally in a data store in the control unit or image analyzer or in a remote system. Additionally or alternatively, if the data is determined by a medical practitioner or software in the control unit, image analyzer or another peripheral computer, to be of clinical interest, it may be logged, or reported to another system or person or other entity. Such reporting may be through any means, including electronic communication, display on a screen, alerting through visual, aural or mechanical means, e.g. displayed as text, sounding an alarm, activating a buzzer or vibrator, sending a text or voice message.

Step 496 is an optional step in which the patient is treated responsive to the results of steps 484, 486 and/or 488. For example, the patient may be provided with additional fluids, salts, vitamins, antioxidants, antibiotics, diuretics, anti-diuretics, medicaments and combinations thereof.

Figure 5:
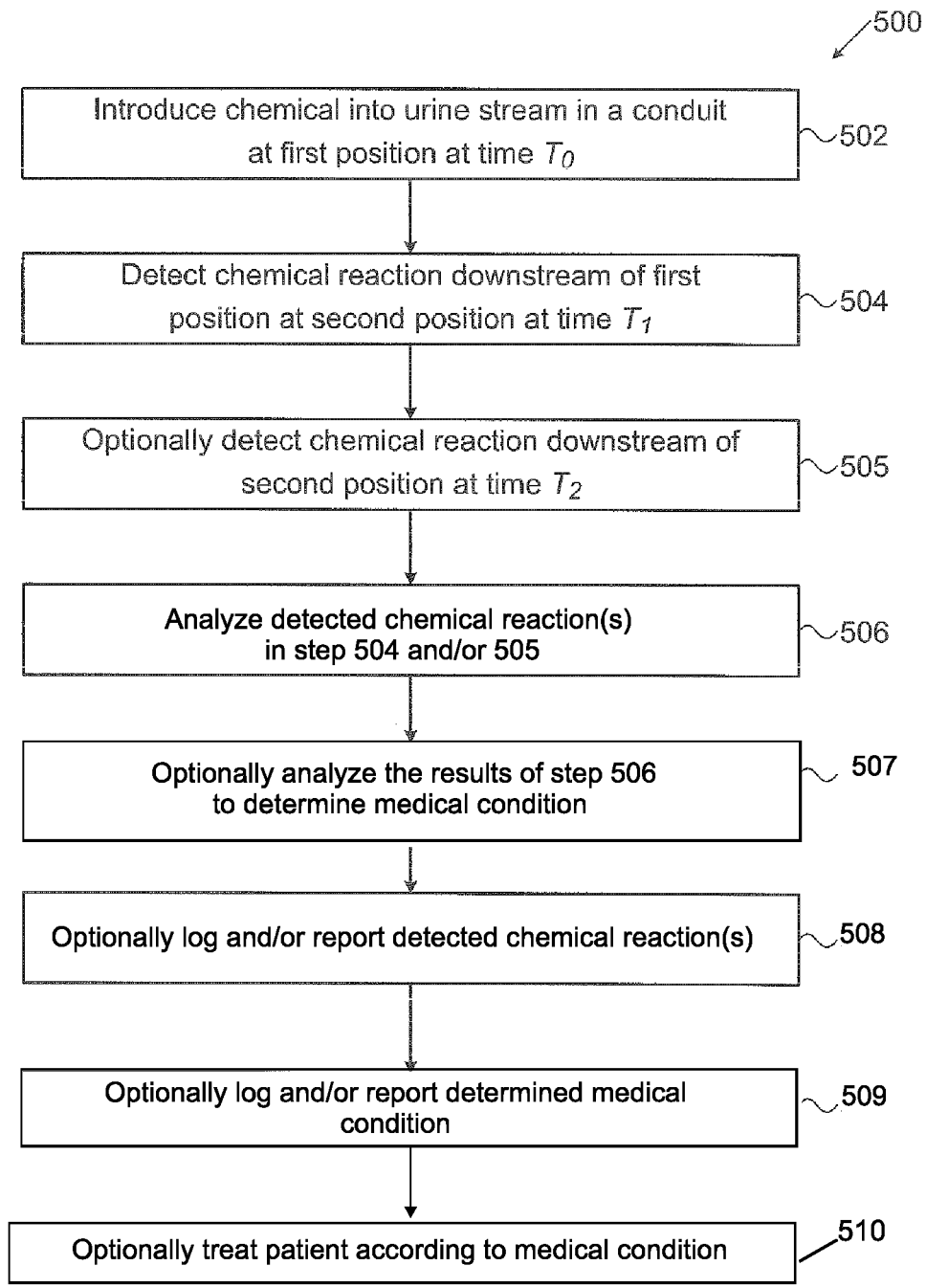
FIG. 5 is a simplified flowchart of a method for inline urine analysis and measurement, in accordance with an embodiment of the present invention.

Reference is now made to FIG. 5, which is a simplified flowchart of a method 500 for inline urine analysis, in accordance with an embodiment of the present invention.

In step 502, the control unit sends instructions to the dispenser 122 to introduce at least one chemical into conduit 108. According to some embodiments, the chemical is selected from the group consisting of a color, a dye, a reactant, a reagent, an indicator, a biochemical and a particulate matter, such as microspheres, nanospheres, nanotubes, powder, etc. According to some embodiments the matter includes inert matter or chemically reactive matter or combinations thereof.

In step 504, at least one control unit, image capture unit and image analyzer are operative to detect at time $T_1$ at least one chemical reaction of the chemical dispensed in step 502 with the urine at a position downstream of the dispenser (for example, by a change in color or other change visible with the naked eye or using magnification and using appropriate illumination such as visible light or ultraviolet light or light of other wavelengths or characteristics such as polarization, collimation, etc.).

Step 505 is an optional step which repeats the actions of step 504 using an image capture unit located further downstream to capture an image after a longer time period has elapsed, i.e., at time $T_2$, thus $T_2>T_1$. Step 505 may optionally be repeated using additional image capture units to capture images at times $T_3$, $T_4$, and so forth.

In a similar fashion, different reaction times can be analyzed by the release of matter from another dispenser at a different distance upstream from an image capture unit.

In step 506, data produced in the at least one image capture unit is analyzed by software in an image analyzer to determine progress or an outcome of a chemical reaction.

Additionally or alternatively, data from the at least one optional image capture unit further downstream is analyzed to detect a chemical reaction taking place after a longer time period $T_2$ (or $T_3$, etc.) has elapsed, or, the subsequent progress of a chemical reaction detected from analysis of one or more earlier images. When analyzing progress of a reaction the analysis may include determination of the rate of the reaction. With appropriate chemicals, a variety of urine properties may be determined as described above. The analysis step is operative on data of at least one image. According to some embodiments a plurality of images from the same or a plurality of image capture units are analyzed to detect chemical reactions.

Step 507 is an optional step in which the results of step 504 and/or step 505 are analyzed by a medical practitioner or software in the image analyzer or a peripheral computer to determine medical conditions and/or potential medical conditions (such as UTI, presence of drugs, pregnancy, diabetes mellitus, kidney failure, liver diseases, glomerulonephritis, hemoglobinuria, ketonuria, etc.), based on the chemical reactions and other data available from the images.

Step 508 is an optional step in which the data gathered in steps 504 and 505 and the results of the analysis in step 506 is logged either locally in a data store in the control unit or analyzer or in a remote system.

Step 509 is an optional step in which, if the data is determined by a medical practitioner or software in the control unit, image analyzer or another peripheral computer, to be of clinical interest, it is logged, or reported to another system or person or other entity. Such reporting may be through any means, including electronic communication, display on a screen, alerting through visual, aural or mechanical means, e.g. displayed as text, sounding an alarm, activating a buzzer or vibrator, sending a text or voice message.

Step 510 is an optional step in which the patient is treated responsive to the results determined in step 506. For example, the patient may be provided with additional fluids, salts, vitamins, antioxidants, antibiotics, diuretics, anti-diuretics, medicaments and combinations thereof.

In various embodiments of the present invention, various components of the apparatus may be partly or fully disposable, or partly or totally reusable (e.g., the image sensor may be a reusable item while some or all of the optical assembly may be part of the disposable item or the image capture unit may be entirely disposable while the control unit is reusable).

Although embodiments of the invention have been described by way of illustration, it will be understood that the invention may be carried out with many variations, modifications, and adaptations, without exceeding the scope of the claims.

The invention claimed is:

1. An apparatus for inline analysis of urine excreted by a patient comprising:
   a. at least one image capture unit being placed along a longitudinal axis of a urinary catheter or a conduit that leads from the urinary catheter to a urine collection container or disposal system, wherein a continuous urine stream flows from the patient to the urine collection container or disposal system continuously through the urinary catheter and wherein the at least one image capture unit is configured to capture images of the continuous urine stream, the at least one image capture unit comprising:
   at least one image sensor configured to capture two-dimensional images and an optical assembly,
   wherein in the at least one image capture unit, the optical assembly focuses light reflected from or transmitted through the continuous urine stream across a field of view of the at least one image capture unit onto the at least one image sensor; and
   b. a control unit operatively connected to all other components of the apparatus by means of a wired or wireless communication channel, the control unit configured to function as an input device that allows manual control, relay of control instructions from peripheral devices or programming of software and processing means in the control unit for automatic control of the at least one image capture unit and any other components of the apparatus and also to function as an output device configured to transfer data related to the images gathered by the at least one image capture unit via wired or non-wired communication channel to peripheral devices;
   wherein, the apparatus is configured to be attached to the urinary catheter that is adapted to be inserted into the patient's bladder or attached to the conduit that leads from the urinary catheter to a urine collection container or disposal system.

2. The apparatus of claim 1, further comprising one or more of each of at least one of the following:
   a. a dispenser configured to dispense different types of matter into the continuous urine stream flowing through the urinary catheter or conduit to aid in analysis of properties of the urine; and
   b. an illumination device configured to be able to illuminate the continuous urine stream flowing across the field of view of the at least one image capture unit through the urinary catheter or conduit.

3. The apparatus of claim 2, further comprising an illumination device, wherein the illumination device is configured to illuminate the continuous urine stream through at least one window in the urinary catheter or conduit such that the light reflected from or transmitted through the continuous urine stream passes through the window or through different windows in the urinary catheter or conduit to be focused by the optical assembly onto the at least one image sensor configured to capture two-dimensional images.

4. The apparatus of claim 1, wherein at least one component of the apparatus is molded or assembled into a wall of a section of the urinary catheter or conduit.

5. The apparatus of claim 1, wherein the at least one image capture unit comprises one of the following:
   a. two polarizing filters to provide data that aids identification of crystals and lipids in the urine;

b. a condenser lens, a waveplate and a neutral density filter to perform contrast phase microscopy to produce data that can be used to identify and analyze cells in the urine;

c. one or more prisms, a diffraction grating or a combination of one or more prisms and a diffraction grating to produce spectroscopic data that can be used to determine an identity and/or concentration of constituents of the urine;

d. two polarizers and a microscope imaging system to provide data that can be used to perform optical mineralogy analysis to identify and analyze crystals in the urine;

e. a diverging lens to provide images that can be used to perform conoscopic analysis to identify and analyze crystals in the urine;

f. an illumination device that emits light of a specific wavelength or wavelengths to cause the urine or objects therein to emit light of a different wavelength and an optical assembly comprising a microscope imaging system that provides data that is used to perform fluorescence microscopy to identify and analyze organic and inorganic matter in the urine;

g. optical components configured to perform OCT (Optical Coherence Tomography) to provide data that is used to obtain high-resolution, 3D, images of particles in the urine.

6. The apparatus of claim 1 wherein the at least one image capture unit comprises at least two image capture units configured in at least one of the following ways:

a. one or more pairs of image capture units configured to yield stereo image pairs; and b. image capture units placed at the same longitudinal position along the urinary catheter or conduit but at different angles in a plane perpendicular to the axis of the urinary catheter or conduit.

7. A system comprising at least one apparatus according to claim 1 and at least one image analyzer unit operatively connected to the at least one image capture unit and/or control unit through a wired or wireless communication channel, the at least one image analyzer unit comprising a processor and software adapted to analyze one or more images captured by the at least one image capture unit to derive information therefrom relating to identification of properties of the urine and/or objects of interest in the continuous urine stream.

8. The system of claim 7, which further incorporates one or more dispenser units, wherein the control unit controls selection and timing of release of matter by the one or more dispenser units and makes the timing information available to the at least one image analyzer unit, which is able to execute a software algorithm adapted to use a distance between the one or more dispenser units and the at least one image capture unit and a comparison of the time of release of said matter to a time of detection by the at least one image capture unit to calculate a rate of travel of the matter in the urinary catheter or conduit.

9. The system of claim 7, wherein at least one component of the system is disposable.

10. A section of a urinary catheter that is adapted to be inserted into a patient's bladder or of the conduit that leads from the urinary catheter to a urine collection container or disposal system, the section comprising at least one component of the apparatus of claim 1 molded or assembled into a wall of the section.

* * * * *